US011408879B2

(12) United States Patent
Owen (10) Patent No.: US 11,408,879 B2
(45) Date of Patent: Aug. 9, 2022

(54) SYSTEM AND METHOD FOR CENTRALIZED WATER MONITORING IN A FISH FARM

(71) Applicant: BLUE UNIT A/S, Odense (DK)

(72) Inventor: David Alexander Owen, Søndersø (DK)

(73) Assignee: BLUE UNIT A/S, Odense (DK)

( * ) Notice: Subject to any disclaimer, the term of this patent is extended or adjusted under 35 U.S.C. 154(b) by 644 days.

(21) Appl. No.: 16/090,865

(22) PCT Filed: Jul. 24, 2017

(86) PCT No.: PCT/DK2017/050248
§ 371 (c)(1),
(2) Date: Oct. 3, 2018

(87) PCT Pub. No.: WO2018/024305
PCT Pub. Date: Feb. 8, 2018

(65) Prior Publication Data
US 2019/0107519 A1    Apr. 11, 2019

(30) Foreign Application Priority Data

Aug. 5, 2016    (DK) ............................ PA 2016 70584

(51) Int. Cl.
*G01N 33/18*    (2006.01)
*A01K 61/10*    (2017.01)
(Continued)

(52) U.S. Cl.
CPC .............. *G01N 33/18* (2013.01); *A01K 61/10* (2017.01); *A01K 63/006* (2013.01); *A01K 63/04* (2013.01); *G01N 33/497* (2013.01)

(58) Field of Classification Search
CPC ...... G01N 33/18; G01N 33/497; A01K 63/04; A01K 63/006; A01K 61/10
See application file for complete search history.

(56) References Cited

U.S. PATENT DOCUMENTS 4,626,992 A * 12/1986 Greaves ............... G01N 33/186
119/268
4,888,703 A * 12/1989 Baba .................... G01N 33/186
702/22
(Continued)

FOREIGN PATENT DOCUMENTS

CN    101281187 A    10/2008
CN    201212888 Y    3/2009
(Continued)

OTHER PUBLICATIONS

International Search Report dated Oct. 2, 2017 for PCT/DK2017/050248.

(Continued)

*Primary Examiner* — Samuel P Siefke
(74) *Attorney, Agent, or Firm* — Schmeiser, Olsen & Watts, LLP (57) ABSTRACT

Provided is a system for centralized water monitoring of a fish farm. the system including a plurality of fish tanks divided into a first and a second subgroup; and a first sample conduit only connected to the first of the subgroups through a first set of pipe connections, and a second sample conduit connected only to the second of the subgroups through a second set of pipe connections; each one of the pipe connections being connected to only one fish tank; the pipe connections being configured for water sampling from a selected fish tank of the first subgroup into the first sample conduit and from a selected fish tank from the second subgroup into the second sample conduit. Water samples are received by a first and second sensor system from the first and second sample conduits for simultaneous measurements of the samples by the sensor system.

11 Claims, 6 Drawing Sheets

(51) Int. Cl.
*A01K 63/04* (2006.01)
*G01N 33/497* (2006.01)
*A01K 63/00* (2017.01)

(56) References Cited

U.S. PATENT DOCUMENTS

| | | | | |
|---|---|---|---|---|
| 6,058,763 | A * | 5/2000 | Shedd | G01N 33/186 |
| | | | | 119/215 |
| 6,093,566 | A * | 7/2000 | Katznelson | A01K 61/00 |
| | | | | 435/287.1 |
| 8,312,768 | B2 | 11/2012 | Duran Neira | |
| 8,534,228 | B2 | 9/2013 | Suedkamp | |
| 2005/0172910 | A1 | 8/2005 | McMillan et al. | |
| 2007/0251461 | A1 | 11/2007 | Reichard et al. | |
| 2010/0099193 | A1 | 4/2010 | Hsu et al. | |
| 2011/0290007 | A1 * | 12/2011 | Sudkamp | A01K 63/00 |
| | | | | 73/60.11 |
| 2013/0009784 | A1 | 1/2013 | Villard | |
| 2014/0261213 | A1 * | 9/2014 | Stiles, Jr. | A01K 63/042 |
| | | | | 119/245 |

FOREIGN PATENT DOCUMENTS

| | | |
|---|---|---|
| CN | 101706493 A | 5/2010 |
| CN | 101713710 A | 5/2010 |
| CN | 102245015 A | 11/2011 |
| CN | 103235097 A | 8/2013 |
| CN | 104007726 A | 8/2014 |
| CN | 203772314 U | 8/2014 |
| CN | 104849418 A | 8/2015 |
| CN | 204579513 U | 8/2015 |
| DE | 19961142 A1 | 7/2000 |
| EP | 2273251 A2 | 1/2011 |
| EP | 2337446 B1 | 6/2011 |
| JP | S576336 | 1/1982 |
| JP | H07120362 A | 5/1995 |
| WO | 2005063006 A1 | 7/2005 |

OTHER PUBLICATIONS

Written Opinion dated Oct. 2, 2017 for PCT/DK2017/050248.
Danish Search Report dated Jan. 12, 2017 for Application No. PA 2016 7054.
International Search Report for PCT/DK2017/050248.
Written Opinion for PCT/DK2017/050248.
Danish Search Report for PCT/DK2017/050248.

* cited by examiner

SYSTEM AND METHOD FOR CENTRALIZED WATER MONITORING IN A FISH FARM

CROSS-REFERENCE TO RELATED APPLICATIONS

This application claims priority to PCT Application No. PCT/DK2017/050248, having a filing date of Jul. 24, 2017, which is based on DK Application No. PA 2016 70584, having a filing date of Aug. 5, 2016, the entire contents both of which are hereby incorporated by reference.

FIELD OF TECHNOLOGY

The following relates to a centralized water monitoring station that provides rapid analysis of water quality for fish farms, for example land-based fish farms. In particular, it relates to a method and system for monitoring water quality in a plurality of fish tanks, especially for centralized water monitoring in a fish farm.

BACKGROUND

Fish today are increasingly cultured in land-based recirculation aquaculture systems (RAS). To ensure optimal fish performance in terms of growth rate, feed conversion and fish welfare, it is critical to ensure a high quality and stable water quality.

Water quality today is managed by a combination of sensors hanging directly in fish farm water and by manual measurements. This solution typically implies that a single fish farm has many decentralized sensors. However, systems with decentralized sensors imply a number of disadvantages. For example, decentralized sensors are difficult and time consuming to calibrate and must be cleaned, typically, by time-consuming manual means. Decentralized sensors also require an expensive electrical installation and result in difficult error detection. Some sensors cannot generate stable and correct results when hanging directly inside a fish tank or water treatment system. For example, some sensors require a stable flow velocity past a measurement membrane to provide a stable measurement. Other sensors can be damaged when they are submerged during a power failure or damaged directly due to mechanical forces.

Furthermore, the sensors used in fish farming today are very susceptible to corruption of data due to bio fouling. Bio fouling on sensing components interferes with readings and often causes false positives, increased noise and sensor failure. When using multiple, decentralized sensors, there are different calibration accuracies for each sensor, varying levels of bio fouling for each sensor, and different physical conditions for each sensor. These differences combine to ensure that the data generated by decentralized sensors are nearly impossible to compare against each other.

There are often multiple fish farms within a single organization. Learning on one farm could be beneficial to the other fish farms within the organization. However, when using multiple, decentralized sensors across multiple fish farms, the number of variables increase to an extent that influences data quality such that data cannot be applied for useful comparison or learning.

In contrast to the above-described decentralized sensors, U.S. Pat. No. 8,534,228 discloses an apparatus with a central measuring device for measuring the water quality for a plurality of fish tanks. Peripheral water conduits from the various fish tanks are connected to a switchable multiplexer, the outlet of which is connected to the central measuring device to selectively feed sample water from each one of the peripheral conduits to the central measurement conduit to test the water in the specific fish tank. Each of two parallel measurement arms of the central measurement conduit comprises multiple sensors connected in series for measurements on water samples from a single fish tank at a time. The water from the fish tanks flows only by gravity to the multiplexer.

The system in U.S. Pat. No. 8,534,228 is a simplification relative to the above mentioned decentralized system. However, it still has some disadvantages. One of the disadvantages is a relatively long measuring time and inferior utilization of the overall measurement capacity, as each water sample has to undergo various measurements, some of which take substantially longer than others, which results in those detectors that finish the measurements quickly to be in an idle state for rather long time while the longer lasting measurements are being done. This is especially so because the system is configured to measure water samples only from a single fish tank at a time. Only once the water samples from a single fish tank are finished, the manifold switches to provide water from another fish tank to the central measurement device. Accordingly, the system is not optimized with respect to speed. To this adds that the gravity flow from the tanks to the measurement device is slow. This is also why the system in the disclosure in U.S. Pat. No. 8,534,228 appears more useful for small-scale fish tank systems than large-scale systems of fish farming where measurement speed has to be optimized. Large-scale systems also require great flexibility in transferring water samples to a centralized water monitoring unit. For example, industrial fish farms have often tanks submerged below the floor surface or in some other way impede the creation of a gravity flow back to a centralized water monitoring unit. Furthermore, a powerful system to evacuate used water samples, remove contaminates from the water sample, and to minimize the effect of small contamination upon the final measurement result are essential when completing centralized measurement on an industrial fish farm.

It would be desirable to provide a system and method that has the advantages of a centralized measurement system but not the disadvantages of the prior art.

SUMMARY

An aspect relates to an improved system for monitoring water quality in fish farms, for example land-based fish farms. This aspect is achieved by a method and system for monitoring water quality in a plurality of fish tanks, especially for centralized water monitoring of a fish farm, as described in more detail in the following.

The following relates to a centralized water monitoring station that is designed for fish farms, for example land-based fish farms, fish farms in ships, or fish farms in open water.

Advantageously, it measures various relevant water quality parameters. The system comprises a first sensor system and a second sensor system for measuring a different parameter, or various different parameters, with the first sensor system as compared to the second sensor system. The inclusion in the design of a dual measurement system maximises the number of water samples that can be measured over the course of a day. This allows the water monitoring station to develop comparable water quality profiles across an entire fish farm with enough detail to help management staff to make significantly improved decisions.

Optionally, the first and second sensor systems are contained in a single building or facility, making a water monitoring station a compact entity.

The method comprises the following step. By the first sensor system, a first sample of water is received from a first of the plurality of fish tanks, and a first parameter of the first sample is measured with the first sensor system. By the second sensor system, a second sample of water is received from a second of the plurality of fish tanks, and a second parameter is measured with the second sensor system. The term first parameter should also be understood as a single first parameter or a set of first parameters. For example, the first sensor system comprises a first set of a plurality of sensors, optionally connected serially or in parallel, by which a first set of parameters is measured in the first sensor system. Correspondingly for the second parameter or parameters.

Advantageously, the second parameter, or second set of parameters, is measured of the second sample with the second sensor system while simultaneously measuring the first parameter, or first set of parameters, of the first sample with the first sensor system. The second parameter is different from the first parameter, thus implying different types of sensors in the first sensor system as compared to the second sensor system.

If the water monitoring station uses two sets of sensors, one set in each sensor system, time is saved by simultaneous measurements of two samples from two different fish tanks by the two sets of sensors.

Once, the two samples are measured, the measurements of the respective sensor systems for the two tanks are reversed, such that, subsequently, another water sample from the second fish tank is received by the first sensor system and the first parameter measured and a further water sample from the first fish tank is received by the second sensor system and the corresponding second parameter measured.

In cases where the measurements for the first and the second sample are done simultaneously, simultaneous measurements are possible but not necessary for the other sample in the first sensor system and the further sample in the second sensor system. This is, especially, so because the time it takes to measure the first parameter with the first sensor system may be substantially longer, for example multiple times longer, than the time it takes to measure the second parameter with the second sensor system. This is the case if the first sensor system comprises a slower sensor or a set of slower sensors, for example for measuring a parameter of at least one of unionized ammonia, carbon dioxide, and total carbonate, and the second sensor system comprises a faster sensor or a set of faster sensors for measuring at least one parameter of oxygen concentration, temperature, redox, turbidity, conductivity, or pH. In such case, the second sensor system can measure several samples during the time it takes for the first sensor system to measure only a single sample.

For example, the water monitoring station uses only one sensor of each type, however, potentially multiple types of sensors in each sensor system. This implies that a higher quality grade of sensor can be afforded and be applied for less cost as for similar systems with multiple sensors of the same type. Applying centralized sensors also makes calibration easier with fewer sensors in one location, especially a central location. Furthermore, using only a single sensor of each type of sensors, especially high-quality sensors, for all measurements means that all results from all measurement locations are directly comparable to each other. Only by accurately benchmarking each measurement location, is it possible to measure the change in water quality across a fish tank. The change in water quality across the fish tank is key to fish performance, with fish performing markedly better when the water environment is stable. By standardizing the quality of data from each water monitoring station, an organization has the ability to benchmark all fish farms against each other.

For example, the system comprises a plurality of fish tanks divided into a first and a second subgroup. A first sample conduit only connects to the first of the subgroups through a first set of pipe connections, and a second sample conduit connects only to the second of the subgroups through a second set of pipe connections. Each one of the pipe connections is connected to only one fish tank. The pipe connections are configured for water sampling from a selected fish tank of the first subgroup into the first sample conduit and from a selected fish tank from the second subgroup into the second sample conduit.

By this system, water samples are received by a first and second sensor system from the first and second sample conduits, respectively, for simultaneous measurements of the two samples by the two-sensor system. In more detail, the system is configured for providing a first water sample selectively from one of the first and second sample conduit to the first sensor system and a second water sample from the other one of the first and second sample conduit to the second sensor system. Measurements of the first parameter of the first sample and the second parameter of the second sample can then be done simultaneously by the first and second sensor system, respectively.

For example, after measuring the second parameter of the second sample, the second sample conduit is emptied, for example by release of pressurized air into the second sample conduit, and a third sample is received by the second sensor system from a third of the plurality of tanks through the second sample conduit. Thus, the second as well as the third sample from two different tanks, and potentially further samples from further tanks, are measured with respect to the second parameter, or second set of parameters, while the first parameter measurement of the first sample is still in progress.

In some embodiments, each one of the first pipe connections comprises a sample point pump for pumping water from the respective fish tank of the first subgroup into the first sample conduit, and each one of the second pipe connections comprises a sample point pump for pumping water from the respective fish tank in the second subgroup into the second sample conduit.

Optionally, each of the pipe connections comprises a water filter and is connected through a valve and filter clean conduit to a source for pressurized air for cleaning the water filter with the pressurized air.

In some embodiments, the samples from either of the two subgroups of fish tanks are provided into two corresponding sample collection chambers, which function as intermediate buffers, one for each subgroup, however, with the freedom to select the sample collection chamber for one or the other subgroup and with the possibility to switch from one subgroup to the other. The sample collection chambers are advantageously larger, for example at least an order of magnitude larger, than the samples taken from them, in order to minimize the variations in samples taken from a single fish tank.

In more detail for a concrete embodiment, a first sample collection chamber is connected to only the first sample conduit for receiving a first water volume from anyone of the fish tanks in the first subgroup into the first sample collection chamber through the first sample conduit. Correspondingly, a second sample collection chamber is connected to only the second sample conduit for receiving a second water volume from anyone of the fish tanks in the second subgroup into the second sample collection chamber through the second sample conduit. The first and second sensor system are selectively connectable to the first and the second sample collection chamber, respectively, for connection of one sensor system to one sample collection chamber while the other sensor system is connected to the other sample collection chamber. This opens the possibility for simultaneous measurements of a first sample from the first sample collection chamber by one sensor system and a second sample from the second sample collection chamber by the other sensor system.

In practice, a first volume of water is collected from the first fish tank via a first sample conduit into a first sample collection chamber and the first sample of water provided to the first sensor from the first sample collection chamber. Further, a second volume of water from the second fish tank is collected via a second sample conduit into a second sample collection chamber, and the second sample of water is provided to the second sensor from the second sample collection chamber. Typically, the amounts of water of the first and second samples are at least an order of magnitude smaller than the first volume and the second volume.

This results in a large, continuous sample flow from the sample delivery system versus a relatively smaller flow of sample water across the sensors. This ensures that a contaminate originating from the tank or sample delivery system, impacts least upon the analysis result.

After, the second sample of water from the second sample collection chamber has been provided to the second sensor, and the second parameter has been measured, the second sample collection chamber and the second sample conduit are emptied, for example by using pressurized air. Subsequently, a third volume of water is collected in the second sample collection chamber via the second sample conduit from a third of the plurality of fish tanks and provided to the second detector system, with a subsequent emptying of the second sample collection chamber from the third volume of water.

In those embodiments, where the time for measuring the first parameter with the first sensor system is multiple times longer than the time for measuring the second parameter with the second sensor system, this measurement of the second and the third sample, optionally including the emptying after measuring the second parameter of the third sample, are done before the measurement of the first parameter of the first sample with the first sensor system is finished.

Advantageously, the cleaning process comprises emptying the second sample collection chamber by releasing pressurized air into the second sample conduit and causing air-pressurized flow of water from the second sample conduit into the second sample collection chamber, followed by emptying the second sample collection chamber through a dump valve. Similarly, the first sample collection chamber and the first sample conduit are emptied with pressurized air, once the measurement of the first parameter in the first water sample has been finalized. Advantageously, the cleaning process comprises flushing the first and second sample conduit with a cleaning agent, for example a sodium hydroxide solution, followed by fresh water flush, and then releasing pressurized air into the first and second sample conduit for pressing the fresh water out of the first and second sample conduit.

A centralized water monitoring system and station, as described, has a number of advantages. It provides the correct water flow velocities for each sensor, and engineers each sensor armature to ensure the correct physical environment under all situations to protect the sensor. For example, the centralized water monitoring station applies automatic cleaning for all sensors and tubes, optionally a combination of compressed air, mechanical washing, ultrasonic cleaning, and chemical cleaning. The sample delivery system for the water monitoring station is configured in such a way as to minimize the distance which the water sample shall travel. This also maximizes the speed and efficiency at which the sample delivery system can be evacuated from used sample water and maximizes the speed at which the sample delivery system can be cleaned. In some embodiments the system provides a full automated cleaning procedure to remove biofilms from every tube, armature and sensor within the entire system.

In some embodiments, the first sensor system comprises a carbon dioxide sensor, CO2 sensor, for indirectly measuring a parameter of total carbonate. The method comprises addition of acid, for example citric acid, to the water sample in order to set carbon dioxide free from the water sample prior to measuring the free carbon dioxide, which is then a measure for the concentration of total carbonates in the water sample.

In some embodiments, the first sensor system comprises an ammonia sensor for measuring a parameter of unionized ammonia, and the method comprises base addition to the water sample prior to measuring the parameter of unionized ammonia.

In some embodiments, the first sensor system comprises a CO2 sensor, for example a standard carbon dioxide probe, for measuring carbon dioxide. Optionally, a breather valve is provided for the CO2 sensor, and opening the breather valve to atmosphere between measurements by the CO2 sensor protects the probe from condensation, and also allows the sensor to drop to a near zero level between measurements. A near zero level between measurements is important to ensure an earlier measurement does not impact upon a future measurement.

In some embodiments, the system comprises a wash manifold that is pipe-connected to sources of cleaning fluids, air, and fresh water and aggregates all the cleaning gases and fluids in a central block of valves. From this central block, any mix of various cleaning fluids, air, and fresh water can be charged at pressure to any selected part of the system, for example selectively to the sample conduits, the sample collection chambers, and the sensor systems.

In some embodiments the system provides the use of pressure relief valves to accelerate the emptying of used sample water from tubes, armatures and sensor heads of the sample delivery system and inside the water monitoring system itself.

For example, each pipe connection is communicating with the water in the fish tank only through a sampling unit that has a water entrance and a water exit, optionally the water exit being at the bottom of the sampling unit. The water entrance has a total entrance area for entrance of water into the sampling unit through the entrance area. The water exit has a total water exit area for exit of water from the sampling unit through the exit area. Advantageous, the entrance area is multiple times larger than the exit area, as this results in a smooth flow into the sampling unit and thereby minimizes the risk for air entering the system. In some embodiment, each pipe connection is communicating with the water in the fish tank only through a sample cup inside the corresponding fish tank, the cup is communicating with the water in the fish tank only through an upward opening below the surface of the water in the fish tank. The upward directed opening prevents air to enter the cup and releases possible air from the cup. Water from the fish tank is sampled into the pipe connection only through the upward opening of the cup. The combination of sample cup and filter is used to exclude gas bubbles and contaminates from water samples collected by the sample delivery system.

Special Remarks to Carbonate Measurements

It should be emphasized that only a small percentage of the free carbon dioxide that is excreted from the fish remains as gaseous free carbon dioxide in the water. The largest portion binds into the water to form carbonate. The percentage that binds is pH dependent—higher the pH the more free carbon dioxide binds into the water. Typically, in fish farm water of pH 7.0, around 90% of the carbon dioxide binds into the water. For example, fish farm water may consist of 100 mg/L total carbonates, of which 10 mg/L remains as free gaseous carbon dioxide and 90 mg/L is bound carbonate. Carbonate is an important chemical to measure as it is responsible for pH stability in the fish tanks, and carbonate is the dominating component of alkalinity in fish farms. Environmental pH is directly important to the physiology of the fish—more stable pH means more stable culture conditions for the fish. The pH also affects the toxicity of a range of chemicals in fish farm water—notably the concentration of gaseous carbon dioxide and the concentration of unionized ammonia.

A problem is the measurement of carbonate for fish farming. As an improvement for measuring carbonate, acid is used, for example citric acid, to lower the pH of the respective water sample. This means that the carbonates in the water sample gets unbound, forming free gaseous carbon dioxide. The free gaseous carbon dioxide is then measured using the carbon dioxide probe.

For this reason also, the above system also provides an embodiment, namely, a method for measuring the total carbonate in water, for example water in a fish tank. The method comprises providing a sample of the water and adding acid, for example citric acid, to the sample to lower the pH of the sample, thereby unbinding carbonate, forming free gaseous carbon dioxide, and measuring the amount of free carbon dioxide with a CO2 sensor. The measured amount of carbon dioxide is then related to the volume of the water sample in order to determine the total carbonate concentration of the water. Optionally, the free carbon dioxide amount for the water is measured prior to the addition of the acid in order to differentiate between free carbon dioxide and bound carbonate in the water.

For a water sample of 100 ml, typically less than 0.1 ml of citric acid is added to free the carbon dioxide from the bound carbonate, where the concentration of the citric acid is 30%, for example in order to lower the pH from 7 to less than pH 4 Alternatively, other acids can be used, for example hydrochloric acid. The concentration and amount of the alternative acid is adjusted to lower the pH from an initial value, for example 7 to less than pH 4.

This embodiment is useful for a fish tank system and advantageously combined with the features of the method and system above.

CO2 Sensor

Common carbon dioxide probes have a CO2 sensor that becomes very hot during operation. This implies that moisture that normally is generated at the air-to-water interface of the probe evaporates into the air. However, when the CO2 sensor after a measurement cools down, when powered off, moisture condenses from the air to form large droplets. When the probe is powered up again subsequently, this moisture enters to the sensor head, causing damage. Especially, the process of stabilizing the carbon dioxide probe between measurements is commonly a very slow process. This means that an earlier measurement can affect the following measurement if an insufficient stabilizing period is not given.

As an example, if a tank 1 had a high free CO2 content of 20 mg/L and tank 2 had a free CO2 content of 10 mg/L, one has to expect about one hour for measuring two tanks, because it would take around 15 minutes to read 20 mg/L, then a stabilizing period of about 30 minutes before the sensor is a sufficiently low level to measure a significantly lower level, and finally around 15 minutes to read 20 mg/L of the second sample.

This is a very slow procedure, why there is a desire for improvements

An improvement can be achieved with a free carbon dioxide probe if the CO2 sensor is combined with a breather valve that provides the CO2 sensor with atmospheric air in order to drain the humidity from the sensor, especially during powering-up. Using such a "breather valve", the process of stabilizing the carbon dioxide probe between measurements is very fast. If a tank 1 had a high free CO2 content of 20 mg/L and tank 2 had a free CO2 content of 10 mg/L, one has to expect only about 30 minutes to measure 2 tanks, which is only half of the time as compared to the foregoing example. The time is distributed to around 15 minutes to read 20 mg/L from tank 1, then a stabilizing period of about 3 seconds, to get the probe back to a zero level, and around 15 minutes to read 20 mg/L. Thus, instead of the prior art 30 minutes stabilizing period, the intermediate period is reduced to three seconds, which is almost instantly.

For this reason, also, the above system also provides an embodiment, namely, a method for measuring free carbon dioxide in water, for example water in a fish tank. In this case a CO2 sensor is provide in combination with a breather valve which in a closed state separates the CO2 sensor from atmospheric air and which in an open state provides a passage from the CO2 sensor to atmospheric air. The method comprises providing a sample of the water and measuring the amount of free carbon dioxide with a CO2 sensor, then opening a breather valve to open a path between the CO2 sensor and atmospheric air and thereby evaporating possible moisture from the CO2 sensor into air, then closing the breather valve again and providing a new sample of water for a subsequent carbon dioxide measurement with the CO2 sensor. For example, the time in which the breather valve is open is less than 1 minute. Thus, the time between measurements can be correspondingly reduced to this time of less than 1 minute.

This embodiment is useful for a fish tank system and advantageously combined with the features of the method and system above. It is also useful when combined with the above method of total carbonate measurement.

BRIEF DESCRIPTION

Some of the embodiments will be described in detail, with references to the following figures, wherein like designations denote like members, wherein:

FIG. 1 shows an overview of the overall system;
FIG. 2 shows details of the analysing system.

DETAILED DESCRIPTION

Referring to FIG. 1, the general scheme of the system is shown. It includes a central monitoring station (00) with analysing mechanism (01) and a sample delivery system (02). Optionally, the central monitoring station is contained in a single building for sake of compactness.

The analysing mechanism (01) is adapted for measuring at least one physical or chemical condition of a water sample. Non-limiting examples of such conditions are free carbon dioxide, oxygen saturation, total gas saturation, temperature, salinity, turbidity, pH, redox potential, and total carbonate.

The knowledge about physical and chemical conditions of the water in fish farms is of utmost importance. Some chemical conditions are directly toxic to fish; some chemical conditions regulate the toxicity of other chemical parameters, while other chemical conditions act as indicators to the health of the water system in general.

Measurement of total carbonates is critical for management of pH across fish tanks. As carbonates strongly buffer pH drops across the fish tank, measurement of total carbonate is essential to manage pH stability in the fish tanks, and subsequently the stability of important toxic chemicals, namely free carbon dioxide and ammonia.

Measurement of unionised ammonia is important as unionised ammonia is the toxic form of ammonia for fish.

The pH of the water is directly important for the health of fish and microbes, affecting internal body processes. The pH of the water also regulates chemical equilibriums for the carbonate and ammonia systems. Toxic free carbon dioxide is released from the carbonate system as pH decreases, while ammonia becomes more toxic with increasing pH.

The oxygen gas saturation in the water is critical for the respiration of fish and microbes; while total gas saturation in the water is important, as super saturated gases can come out of solution and form gas bubbles within the fish, causing stress and mortality. The turbidity is an indicator for negative trends and also directly damages fish's gills.

Salinity and temperature affect gas saturation in water, are important for internal body processes for both fish and microbes and can affect the toxicity of some compounds. The redox potential of water acts as an indicator of toxic substances and an indicator of the health of the water system in general.

The analysing mechanism is physically divided into two sub-units, wherein one sub-unit comprises fast sensors (24) and another sub-unit comprises slow sensors (26) where the fast sensors are doing the measurements faster than the slow sensors. At any one moment, one water sample is directed to the slow sensor group, which belongs to a first sensor system, while the other water sample is directed towards the fast sensor group, which is a second sensor system. This dual measurement system ensures that the slow measurement sequence does not act as a bottleneck to the fast measurement sequence. In this way, a sequence of fast measurements from multiple fish tanks can be achieved during the time it takes for a single slow measurement. This is in contrast to the aforementioned disclosure of U.S. Pat. No. 8,534,228 in which only water samples from a single fish tank can be measured at a time, despite using two lines of different sensors in parallel.

A dual measurement system maximises the speed of the analysing mechanism and, thus, maximises the number of water samples that can be measured over the course of a day. In this way the water monitoring station can develop comparable water quality profiles across an entire fish farm with enough detail to make significantly improved management decisions.

Component Description

The sample delivery system (02) has two parallel lines of sample points 1 to 6 (04) and sample points 7 to 12 (06). Sample points 1-6 deliver water samples to sample conduit 1 (08), while sample points 7-12 deliver water sample to sample conduit 2 (10). The first sample conduit (08) is flow-connected to a first sample chamber (12), and the second sample conduit (10) is flow-connected to a second sample chamber (14).

Figure 5A:
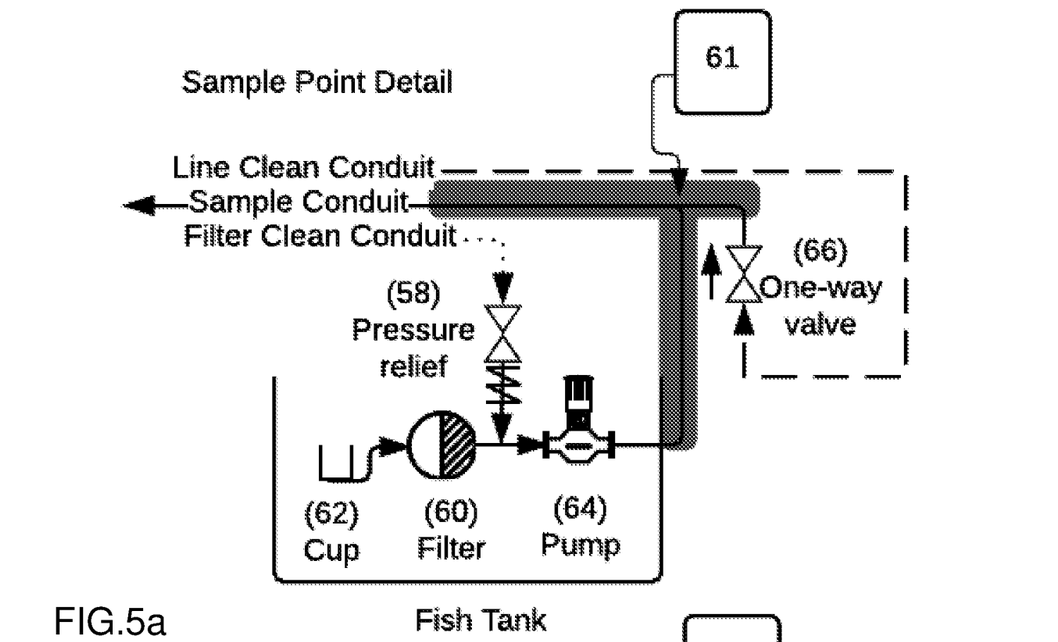
FIG. 5a shows a first variation of a sample point, depending upon the installation.
Figure 5B:
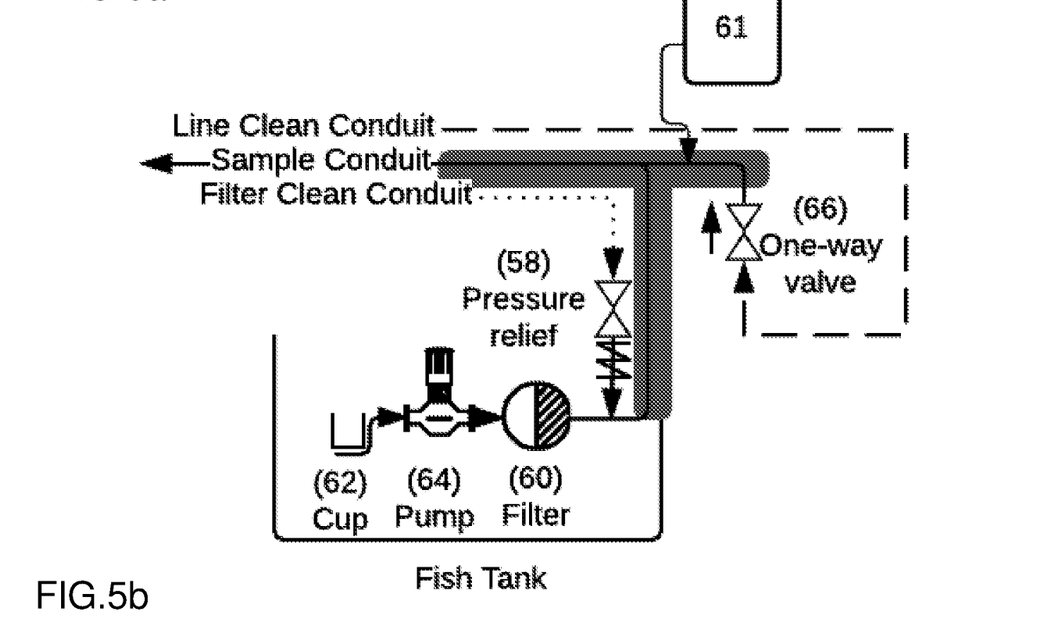
FIG. 5b shows a first variation of a sample point, depending upon the installation.

Reference is made to FIG. 5 showing the fish tank of FIG. 1 in greater detail. When a sample point pump (60) is activated, receiving a sample from cup (62), it delivers sample water, filtered by filter (60), to an internal manifold (61) (FIG. 5). One side of the manifold connects directly with the sample conduit (08 or 10), extending proximally to the sample chambers (12) and (14) illustrated in FIG. 1. The other side of the internal manifold has a one-way valve (66) that connects directly with the sample conduit extending distally to the next sample point with a cup (62). Alternatively, if the fish tank has the last sample point on a sample conduit (08 or 10), the one-way valve (66) represents the last point of attachment (67) of the line clean conduit (56.2 or 56.4) as best seen in FIG. 1.

This configuration ensures that the water sample flows only from a distal to proximal direction, along the sample conduit (08 or 10) to the sample collection chambers (12, 14) of the central monitoring station (00). This represents the most direct sample delivery solution, minimizing the distance the water sample shall travel, and maximizes the speed and efficiency at which the sample delivery system can be evacuated of used sample water, and maximizes the speed at which the sample delivery system can be cleaned.

Sample conduit 1 delivers water sample via a non-return valve to sample collection chamber 1 (12) of the central monitoring station. Sample conduit 2 delivers water sample via a non-return valve to sample collection chamber 2 (14) of the central monitoring station. Both sample collection chambers are non-pressurize. This means they are exposed to atmospheric air pressure only. When the sample collection chambers are full, excessive water sample flows to waste via surface overflow outlets (15).

The flow from the sample points (04, 06) is multiple times larger than the sample drawn across the sensors (24, 26). This ensures that any air bubbles or anything else that could contaminate the water sample is diluted out before it is analysed by the sensors.

A partial flow of water sample is drawn from sample collection chamber 1 via pump 1 (16) and delivered to selector valve 1 (18). A partial flow of water sample is drawn from sample collection chamber 2 via pump 2 (20) and delivered to selector valve 2 (22).

The partial water sample flow at selector valve 1 can either be fully directed to the fast sensors (24) or to the slow sensors (26) of the analysing mechanism. The partial water sample flow at selector valve 2 can either be fully directed to the fast sensors (24) or to the slow sensors (26).

Water sample being directed to the fast sensors (24) via either one of the selector valves (18, 22) first enters fast sensor armature 1, then armature 2 and finally armature 3 (28); a serial flow pattern (FIG. 2). For example, up to three sensors can be inserted into each armature, giving nine sensors in all. A partial flow is also delivered to a turbidity sensor (30), which requires a lower flow velocity for optimal performance. After flowing across the sensors, water is discharged to waste.

Water sample being directed to the slow sensors via either one of the selector valves first enters to the carbon dioxide sensor (32) and finally armature 4 (34). Again, a serial flow pattern (FIG. 2). For example, up to three sensors can be inserted into armature 4. An air breather valve (36) allows the carbon dioxide sensor to open to the atmospheric air. After flowing across the sensors, water is discharged to waste.

Figure 4:
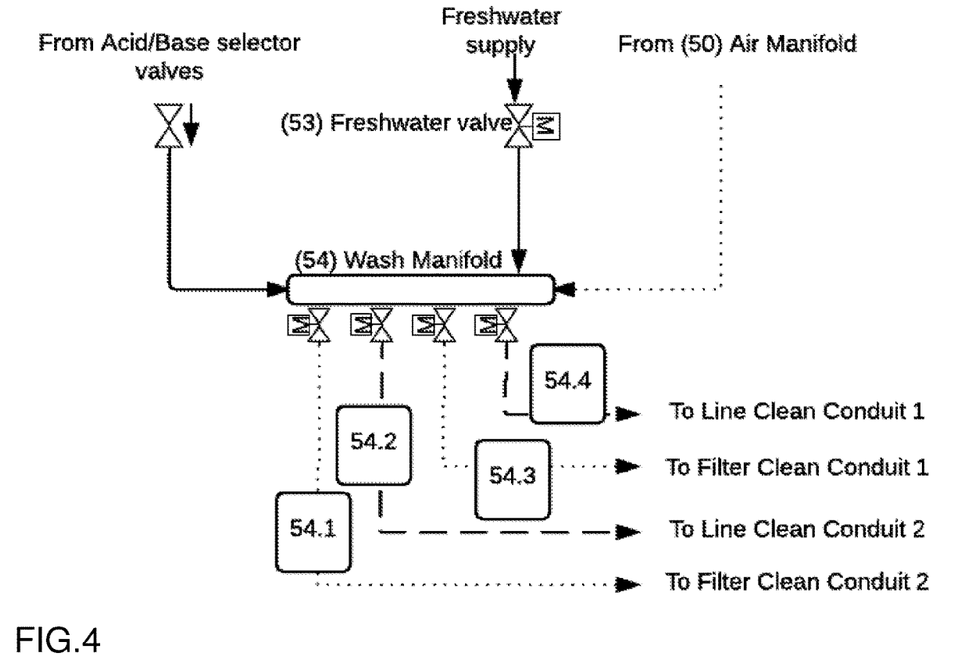
FIG. 4 shows the cleaning manifold in greater detail.

Citric acid is drawn from an acid reservoir via an acid pump (38) and discharges to an acid selector valve (40). Under normal operation, acid is delivered to the water sample being directed to the slow sensors (26), before the carbon dioxide probe. Under a cleaning operation, the acid selector valve (40) is activated and discharges acid to the wash manifold (54) (FIG. 4).

Sodium hydroxide is drawn from a base reservoir via a base pump (42) and discharges to a base selector valve (44). Under normal operation, base is delivered to the water sample being pumped to the slow sensors, after the carbon dioxide probe, but before armature 4. Under a cleaning operation, the base selector valve is activated and discharges base to the wash manifold (54) (FIG. 4).

Figure 3:
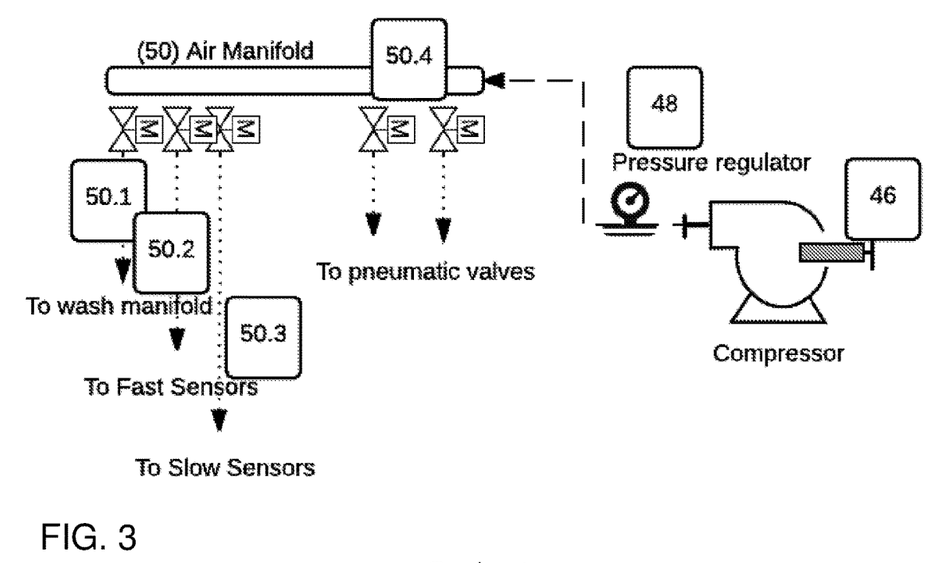
FIG. 3 shows the air manifold in greater detail.

A compressor (46) generates the air for an air manifold, regulated automatically to maintain elevated pressure, for example 6 bar, using a pressure regulator (48). The air manifold (50) (FIG. 3) comprises 4 valves. The first valve (50.1) delivers compressed air to a wash manifold. The second valve (50.2) delivers compressed air to the fast sensors. The third valve (50.3) delivers compressed air to the slow sensors. The air manifold also delivers air to a set of pneumatic valves (50.4).

Compressed air being delivered to the fast and slow sensors pressurizes the water inside the system. Each sensor armature has a pressure relief valve of 2 bar at its base (51), see FIG. 2. When pressure inside the sensor and armature bodies exceeds 2 bar, the sample water is rapidly evacuated from the sensors and armature bodies via the pressure relief valves (51), discharging the sample water to waste.

The pneumatic valves (52.1 and 52.2 respectively) control the water level of the water sample collection chambers (FIG. 1). When dump valve 1 (52.1) is open, the water of sample collection chamber 1 is discharged to waste. When dump valve 2 (52.2) is open, the water of sample collection chamber 2 is discharged to waste.

A freshwater valve (53) is installed to deliver freshwater at pressure to the wash manifold.

The wash manifold (54) (FIG. 4) comprises four valves each delivering either air, freshwater or freshwater mixed with chemical (acid or base). The first valve (54.1) of the wash manifold delivers its washing mix to filter clean conduit 2. The second valve (54.2) of the wash manifold delivers its washing mix to line clean conduit 2. The third valve (54.3) of the wash manifold delivers its washing mix to filter clean conduit 1. The fourth valve (54.4) of the wash manifold delivers its washing mix to line clean conduit 1. The wash manifold, optionally comprises further valves for further fluids.

When a valve of the wash manifold (54) is activated, either air or freshwater or a mix of freshwater with chemical (acid or base) is delivered to the cleaning conduits (56) at high pressure (4-6 bar). When a cleaning mix is delivered to filter clean conduit 1 (56.1) or filter clean conduit 2 (56.3), the sample point pressure relief valves (58) open (FIG. 5). This charges air at 4-6 bar into each sample point filter (60) and the sample cup (62), removing old sample water and any detritus that could interfere with the sampling process.

When a cleaning mix is delivered from the wash manifold to either line clean conduit 1 (56.2) or line clean conduit 2 (56.4), the cleaning mix is charged at 4-6 bar into either sample conduit 1 or sample conduit 2. The high-pressure cleaning mix rapidly displaces old sample water back to the sample collection chambers of the central monitoring station.

Sample points (FIG. 5) can be configured differently depending upon the installation location. Each sample point comprises of a sample point cup (62), a sample point filter (60), a sample point pump (64), a sample point pressure relief valve (58), and a sample point one-way valve (66).

The sample cup ensures no air bubbles can be drawn into the sample point pump. The sample filter ensures no detritus can enter to the water sample. The sample point pump can either suck, push, or a combination of the two to pressurize the water sample just enough to deliver water sample to the non-pressurized sample collection chambers of the central monitoring station.

Sequence Description

The entire sampling and measurement process is controlled by a programmable logic controller (PLC) (68). The PLC can directly send out alert signals to a recipient user or controller. The PLC is server configured to receive input information from users in the form of threshold data.

The PLC compares utility data (level of a physical or chemical condition of a water sample) and threshold data to determine whether utility data exceeds a predetermined threshold in threshold data. The server is programmed to access the data from the analysing mechanism on a nearly continuous basis. The server can then generate and transmit graphical displays of data and alerts as appropriate though a network, e.g. internet, to recipient devices.

The processes of measuring unionized ammonia, carbon dioxide and total carbonate are relatively slow, taking for example 30 minutes. The remaining measurements including oxygen, temperature, redox, turbidity, conductivity, and pH are fast measurements, taking for example 5 minutes.

To ensure that the slow measurement sequence does not act as a bottleneck to the fast measurement sequence, the hardware and software sequence takes in two water samples in parallel. One water sample is directed to the slow sensor group, while the other water sample is directed towards the fast sensor group. In this way, a sequence of 6 fast measurements can be achieved for a single slow measurement.

The PLC initiates the operation of a single sample point pump on sample conduit 1 (1 to 6 sample points) and a single sample point pump on sample conduit 2 (7 to 12 sample points). Water samples fill sample collection chambers 1 and 2 respectively (12 and 14) of the central monitoring station.

At the start of a sequence, dump valve 1 (52.1) and dump valve 2 (52.2) are open, discharging the both water samples to waste. This is an effective flushing of contaminates out of the system. Once contaminates are flushed the dump valves close and the sample collection chambers are filled, with excessive water sample flowing to waste via surface overflow outlets (15).

A partial flow of water sample is continually drawn from each of the sample collection chambers via pump 1 (16) and pump 2 (20). Selector valve 1 (18) directs water sample from sample collection chamber 1 to either fast sensors (24) or to slow sensors (26). Selector valve 2 (22) directs water sample from sample collection chamber 2 to the opposite sensor group than selector valve 1.

Fast Sensor Sequence

Water sample being directed to the fast sensors via either one of the selector valves first enters to fast sensor armature 1, then armature 2 and finally armature 3 (28); a serial flow pattern (FIG. 2). After several minutes of flushing with water sample, the fast sensors begins to log the values of the water sample to the data logger of the PLC.

Following logging, the sample collection chamber is discharged of used water sample by the associated dump valve. Meanwhile the first valve (50.1) of the air manifold pressurises the wash manifold with 6 bar of compressed air.

Where sample conduit 2 most recently delivered water sample to the fast sensors, the first valve (54.1) of the wash manifold is activated for several seconds, charging compressed air to filter clean conduit 2. Alternatively, if sample conduit 1 most recently delivered water sample to the fast sensors, the third valve (54.3) of the wash manifold is activated for several seconds, charging compressed air to filter clean conduit 1.

When compressed air enters either filter clean conduits, the sample point pressure relief valves (58) of each sample point opens, charging air at 4-6 bar into each sample point filter (60) and the sample cup (62) (FIG. 5). This removes old sample water and any detritus that could interfere with the sampling process.

Following cleaning of the filter clean conduits, the line clean conduits are pressurised. Where sample conduit 2 most recently delivered water sample to the fast sensors, the second valve (54.2) of the wash manifold is activated for several seconds, charging compressed air to line clean conduit 2. Alternatively, if sample conduit 1 most recently delivered water sample to the fast sensors, the fourth valve (54.4) of the wash manifold is activated for several seconds, charging compressed air to line clean conduit 1.

When compressed air enters either line clean conduits, the 4-6 bar air is charged into either sample conduit 1 or sample conduit 2. The high-pressure air rapidly displaces old sample water back to the sample collection chambers of the central monitoring station, from where it discharges to waste.

The final part of the fast sensor sequence is evacuating all the old sample water from the tubes and armatures inside the central monitoring station. The second valve (50.2) of the air manifold delivers compressed air to the fast sensor group, pressurizing the fast sensor system. Each sensor armature has a pressure relief valve of 2 bar at its base (51). When pressure inside the sensor and armature bodies exceeds 2 bar, the sample water is rapidly evacuated out of the sensors and armature bodies via the pressure relief valves, discharging the sample water to waste.

The PLC then triggers the next sample point pump of the same sample conduit to activate, continuing the fast measurement sequence. Once all sample points are measured on a single sample conduit, the PLC switches the fast sequence to continue on the opposite sample conduit of the delivery system.

Slow Sensor Sequence

Water sample being directed to the slow sensors via either one of the selector valves first enters to the carbon dioxide sensor (32) and finally armature 4 (34). Again, a serial flow pattern (FIG. 2). An air breather valve (36) opens to ambient atmosphere at the start of every slow measurement sequence to ensure the carbon dioxide sensor is not exposed to any condensation that may have formed inside the sensor measurement tubes, and also allows the sensor to fall to a near zero reading within a very short time, for example in the range of less than 1 minute, typically only 1-10 seconds. This prevents an earlier measurement influencing a future measurement, while still minimizing measurement time.

The slow sensor measurement sequence is broken into two phases—a high sample pH phase followed by a low sample pH phase. The high sample pH is achieved with base (sodium hydroxide) dosing dropwise, while the low sample pH is achieved with citric acid dosing dropwise.

The high sample pH phase begins when sodium hydroxide is drawn from a base reservoir via a base pump (42) and discharges to a base selector valve (44). During the slow measurement sequence, base is delivered dropwise to the water sample being pumped to the slow sensors, after the carbon dioxide probe, but before armature 4. When the water sample is raised in pH all forms of ammonia that may be present in the water sample convert to the unionised form (NH3). By doing this, the concentration of measurement substance increases by more than 10-fold. As a result, an NH3 probe located in armature 4 does not need to rely on measuring very small amounts of NH3 easily affected by contamination, but can rather measure 10-fold greater concentrations.

During the final minutes of the high pH phase of the slow sensor sequence, the values of carbon dioxide and total unionised ammonia are logged by the data logger of the PLC. A unique log pattern can be programmed for each sensor.

The low sample pH phase begins when citric acid is drawn from an acid reservoir via an acid pump (38) and discharges to an acid selector valve (40). During the slow sensor measurement sequence, acid is delivered dropwise to the water sample being directed to the slow sensors, before the carbon dioxide probe. Acidification of the sample allows measurement of total carbonates of the water sample in the carbon dioxide probe.

During the final minutes of the low pH phase of the slow sensor sequence, the values of total carbonate are logged by the data logger of the PLC. A unique log pattern can be programmed for each sensor.

Only a small percentage of the free carbon dioxide that is excreted from the fish remains as gaseous free carbon dioxide in the water. The largest portion binds into the water to form carbonate. The amount that binds is pH dependent—higher the pH the more free carbon dioxide binds into the water. Acidification of the water sample to the free carbon dioxide probe ensures that 99% of the carbonate that is bound in the water becomes free carbon dioxide.

Following logging, the sample collection chamber is discharged of used water sample by the associated dump valve. Meanwhile the first valve (50.1) of the air manifold pressurises the wash manifold with 6 bar of compressed air.

Where sample conduit 2 most recently delivered water sample to the slow sensors, the first valve (54.1) of the wash manifold is activated for several seconds, charging compressed air to filter clean conduit 2. Alternatively, if sample conduit 1 most recently delivered water sample to the slow sensors, the third valve (54.3) of the wash manifold is activated for several seconds, charging compressed air to filter clean conduit 1.

When compressed air enters either filter clean conduits, the sample point pressure relief valves (58) of each sample point opens, charging air at 4-6 bar into each sample point filter (60) and the sample cup (62) (FIG. 5). This removes old sample water and any detritus that could interfere with the sampling process.

Following cleaning of the filter clean conduits, the line clean conduits are pressurised. Where sample conduit 2 most recently delivered water sample to the slow sensors, the second valve (54.2) of the wash manifold is activated for several seconds, charging compressed air to line clean conduit 2. Alternatively, if sample conduit 1 most recently delivered water sample to the slow sensors, the fourth valve (54.4) of the wash manifold is activated for several seconds, charging compressed air to line clean conduit 1.

When compressed air enters either line clean conduits, the 4-6 bar air is charged into either sample conduit 1 or sample conduit 2. The high-pressure air rapidly displaces old sample water back to the sample collection chambers of the central monitoring station, from where it discharges to waste.

The final part of the slow sensor sequence is evacuating all the old sample water from the tubes and armatures inside the central monitoring station. The third valve (50.3) of the air manifold delivers compressed air to the slow sensor group, pressurizing the slow sensor system. Sensor armature 4 has a pressure relief valve of 2 bar at its base (51). When pressure inside the sensor and armature bodies exceeds 2 bar, the sample water is rapidly evacuated out of the sensors and armature bodies via the pressure relief valves, discharging the sample water to waste.

Once a single sample point is measured on a single sample conduit, the PLC switches the slow sequence to continue on the opposite sample conduit of the delivery system.

Cleaning Sequence

Applying a chemical cleaning process ensures no biofilm build-up on sensor heads or tubes. This saves cleaning time, and avoids mechanical cleaning by the human hand that can risk damaging the sensors. The configuration of the sample delivery system maximises the speed of the cleaning process.

The PLC (68) controls the cleaning sequence. The cleaning sequence can be initiated automatically (eg 1 time per day), or by a user triggering a locally placed switch.

Sodium hydroxide is drawn from a base reservoir via a base pump (42) and discharges to a base selector valve (44). During the cleaning sequence, base is delivered dropwise to the wash manifold.

The wash manifold (54) (FIG. 4) comprises of four valves. The first valve (54.1) of the wash manifold is initially opened to allow the base being dosed to flow slowly to filter clean conduit 2. After some minutes the freshwater valve (53) is activated allowing freshwater to enter the wash manifold and subsequently the filter clean conduit 2 under pressure.

When a cleaning mix is delivered to filter clean conduit 2 (56.3), the sample point pressure relief valves (58) open (FIG. 5). This charges a basic cleaning solution at 4-6 bar into each sample point filter (60) and the sample cup (62), lining all surfaces. The freshwater valve is then deactivated.

The third valve (54.3) of the wash manifold is then opened to allow the base being dosed to flow slowly to filter clean conduit 1. After some minutes the freshwater valve (53) is activated allowing freshwater to enter the wash manifold and subsequently the filter clean conduit 2 under pressure.

When a cleaning mix is delivered to filter clean conduit 1 (56.1), the sample point pressure relief valves (58) open (FIG. 5). This charges a basic cleaning solution at 4-6 bar into each sample point filter (60) and the sample cup (62), lining all surfaces. The freshwater valve is then deactivated.

The second valve (54.2) of the wash manifold is then opened to allow the base being dosed to flow slowly to line clean conduit 2. After some minutes the freshwater valve (53) is activated allowing freshwater to enter the wash manifold and subsequently the line clean conduit 2 under pressure.

When a cleaning mix is delivered to line clean conduit 2 (56.4), the basic cleaning solution is charged at high pressure to rapidly displace old sample water back to the sample collection chambers of the central monitoring station. The freshwater valve is first deactivated when it is certain that sample collection chamber 2 (14) is filled with the basic solution.

The fourth valve (54.4) of the wash manifold is then opened to allow the base being dosed to flow slowly to line clean conduit 1. After some minutes the freshwater valve (53) is activated allowing freshwater to enter the wash manifold and subsequently the line clean conduit 2 under pressure.

When a cleaning mix is delivered to line clean conduit 1 (56.2), the basic cleaning solution is charged at high pressure to rapidly displace old sample water back to the sample collection chambers of the central monitoring station, lining all surfaces. The freshwater valve is first deactivated when it is certain that sample collection chamber 1 (12) is filled with the basic solution.

Once all conduits and sample collection chambers are filled with a basic solution, the entire system is allowed to stand for 15 minutes, in order for the basic solution to destroy any biofilm that may be present. Following this an acid treatment is commenced.

Citric acid is drawn from an acid reservoir via an acid pump (38) and discharges to an acid selector valve (40). During the cleaning sequence, acid is delivered dropwise to the wash manifold.

The wash manifold (54) (FIG. 4) comprises of four valves. The first valve (54.1) of the wash manifold is initially opened to allow the acid being dosed to flow slowly to filter clean conduit 2. After some minutes the freshwater valve (53) is activated allowing freshwater to enter the wash manifold and subsequently the filter clean conduit 2 under pressure.

When a cleaning mix is delivered to filter clean conduit 2 (56.3), the sample point pressure relief valves (58) open (FIG. 5). This charges an acidic cleaning solution at 4-6 bar into each sample point filter (60) and the sample cup (62), lining all surfaces. The freshwater valve is then deactivated.

The third valve (54.3) of the wash manifold is then opened to allow the acid being dosed to flow slowly to filter clean conduit 1. After some minutes the freshwater valve (53) is activated allowing freshwater to enter the wash manifold and subsequently the filter clean conduit 1 under pressure.

When a cleaning mix is delivered to filter clean conduit 1 (56.1), the sample point pressure relief valves (58) open (FIG. 5). This charges an acidic cleaning solution at elevated pressure, for example 4-6 bar, into each sample point filter (60) and the sample cup (62), lining all surfaces. The freshwater valve is then deactivated.

The second valve (54.2) of the wash manifold is then opened to allow the acid being dosed to flow slowly to line clean conduit 2. After some minutes the freshwater valve (53) is activated allowing freshwater to enter the wash manifold and subsequently the line clean conduit 2 under pressure.

When a cleaning mix is delivered to line clean conduit 2 (56.4), the acidic cleaning solution is charged at high pressure to rapidly displace old sample water back to the sample collection chambers of the central monitoring station. The freshwater valve is first deactivated when it is certain that sample collection chamber 2 (14) is filled with the acidic solution.

The fourth valve (54.4) of the wash manifold is then opened to allow the acid being dosed to flow slowly to line clean conduit 1. After some minutes the freshwater valve (53) is activated allowing freshwater to enter the wash manifold and subsequently the line clean conduit 1 under pressure.

When a cleaning mix is delivered to line clean conduit 1 (56.2), the acidic cleaning solution is charged at high pressure to rapidly displace old sample water back to the sample collection chambers of the central monitoring station, lining all surfaces. The freshwater valve is first deactivated when it is certain that sample collection chamber 1 (12) is filled with the acidic solution.

Once all conduits and sample collection chambers are filled with an acidic solution, the entire system is allowed to stand for 10 minutes, in order for the acidic solution to neutralize any base residues that maybe present. Following this the entire system is flushed with freshwater.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

REFERENCE NUMBERS

00 Central monitoring station
01 Analysing mechanism
02 Sample delivery system
04 Sampling points 1-6 in first subgroup of fish tanks
06 Sampling points 7-12 in second subgroup of fish tanks
08 Sample Conduit 1
10 Sample Conduit 2
12 First sample chamber
14 Second sample chamber
15 Surface overflow outlets
16 Pump 1
18 Selector Valve 1
20 Pump 2
22 Selector Valve 2
24 Sub-unit 1 of analysing mechanism—Fast Sensors
26 Sub-unit 2 of analysing mechanism—Slow Sensors
28 Fast sensor armatures 1, 2 and 3
30 Turbidity Sensor
32 Carbon dioxide Sensor
34 Slow Sensor armature 4
36 Air breather valve
38 Acid pump
40 Acid selector valve
42 Base pump
44 Base selector valve
46 Compressor
48 Pressure regulator
50 Air manifold
50.1 Air valve to the wash manifold
50.2 Air valve to the fast sensors
50.3 Air valve to the slow sensors
50.4 Air to the pneumatic valves
51 Armature pressure relief valve
52 Pneumatic Valves
52.1 Dump valve 1
52.2 Dump valve 2
53 Freshwater valve
54 Wash Manifold
54.1 Valve to filter clean conduit 2
54.2 Valve to line clean conduit 2
54.3 Valve to filter clean conduit 1
54.4 Valve to line clean conduit 1
56 Cleaning Conduits
56.1 Filter clean conduit 1
56.2 Line clean conduit 1
56.3 Filter clean conduit 2
56.4 Line clean conduit 2
58 Sample point pressure relief valve
60 Sample point filter
61 Internal manifold
62 Sample cup
64 Sample point pump
66 Sample point one-way valve
67 Line clean conduit point of attachment to sample conduit
68 Programmable logic controller (PLC)

The invention claimed is:

1. A method for centralized monitoring of water quality in a plurality of fish tanks, wherein the method comprises:
providing a central monitoring station having a first sensor system and a second sensor system, wherein the first sensor system and second sensor system are located remotely with respect to the plurality of fish tanks;
receiving, by the first sensor system, a first sample of water from a first of the plurality of fish tanks through a first sample conduit and measuring a first parameter of the first sample by the first sensor system, wherein the first parameter represents a physical or chemical condition of the first sample of water;
receiving, by the second sensor system, a second sample of water from a second of the plurality of fish tanks through a second sample conduit and measuring a second parameter by the second sensor system while simultaneously measuring the first parameter of the first sample by the first sensor system, wherein the second parameter represents a physical or chemical condition of the second sample of water and the second parameter is different from the first parameter; and
subsequently receiving another water sample from the second fish tank by the first sensor system through the second sample conduit and measuring the first parameter thereof and receiving a further water sample from the first fish tank by the second sensor system through the first sample conduit and measuring the corresponding second parameter thereof.

2. The method according to claim 1, wherein the time for measuring the first parameter with the first sensor system is multiple times longer than the time for measuring the second parameter with the second sensor system; wherein the method comprises after measuring the second parameter by the second sensor system, receiving a third sample water from a third of the plurality of fish tanks by the second sensor system and measuring the second parameter of the third sample with the second sensor system while still in the process of measuring the first parameter of the first sample with the first sensor system.

3. The method according to claim 1, wherein the plurality of fish tanks is divided into a first subgroup and a second subgroup; wherein the method comprises receiving the first sample of water by the first sensor system through the first sample conduit that through a first set of pipe connections is connected only to the first of the subgroups, and receiving the second sample of water by the second sensor system through the second sample conduit through a second set of pipe connection that is connected only to the second of the subgroups; wherein each one of the pipe connections is connected to only one fish tank; wherein the method comprises after measuring the second parameter of the second sample, emptying the second sample conduit, and receiving a third sample by the second sensor system through the second sample conduit from a third of the plurality of tanks through the second sample conduit; wherein the first fish tank belongs to the first subgroup and the second and third fish tanks to the second subgroup.

4. The method according to claim 3, wherein the method comprises emptying the second sample conduit by release of pressurized air into the second sample conduit.

5. The method according to claim 3, wherein each one of the first pipe connections comprises a sample point pump for pumping water from the respective fish tank of the first subgroup into the first sample conduit, and wherein each one of the second pipe connections comprises a sample point pump for pumping water from the respective fish tank in the second subgroup into the second sample conduit.

6. The method according to claim 1, wherein the method comprises collecting a first volume of water from the first fish tank via a first sample conduit into a first sample collection chamber and providing the first sample of water to the first sensor from the first sample collection chamber; collecting a second volume of water from the second fish tank via a second sample conduit into a second sample collection chamber and providing the second sample of water to the second sensor from the second sample collection chamber; wherein the amount of water of the first and second samples are at least an order of magnitude smaller than the first volume and the second volume.

7. The method according to claim 6, wherein the time for measuring the first parameter with the first sensor system is multiple times longer than the time for measuring the second parameter with the second sensor system; wherein the method comprises providing the second sample of water from the second sample collection chamber to the second sensor and measuring the second parameter of the second sample with the second sensor system, emptying the second sample collection chamber and the second sample conduit, and subsequently collecting a third volume of water in the second sample collection chamber via the second sample conduit from a third of the plurality of fish tanks and providing the third sample to the second detector system and measuring the second parameter of the third sample with the second sensor system prior to finalizing the measurement of the first parameter of the first sample with the first sensor system.

8. The method according to claim 7, wherein the method comprises emptying the second sample collection chamber by releasing of pressurized air into the second sample conduit and causing air-pressurized flow of water from the second sample conduit into the second sample collection chamber, and emptying the second sample collection chamber through a dump valve.

9. The method according to claim 4, wherein the method comprises flushing the second sample conduit with a base solution, followed by an acid solution, followed by fresh water and then releasing pressurized air into the second sample conduit for pressing the fresh water out of the second sample conduit.

10. The method according to claim 1, wherein the first sensor system comprises a CO2 sensor for measuring free carbon dioxide, and wherein the method comprises adding acid to the first water sample for setting free carbon dioxide from the water sample prior to measuring the free carbon dioxide and thereby obtaining a measure for the total carbonate concentration in the water sample.

11. The method according to claim 1, wherein the first sensor system comprises a CO2 sensor for measuring carbon dioxide and a breather valve between the CO2 sensor and atmosphere, and wherein the method comprises opening the breather valve between subsequent measurements for providing a connection from the CO2 sensor to ambient atmosphere, allowing humidity to leave the CO2 sensor prior to a subsequent measurement of carbon dioxide.

* * * * *